United States Patent
Charraud et al.

(10) Patent No.: US 12,102,207 B2
(45) Date of Patent: Oct. 1, 2024

(54) ROLLER BALL APPLICATOR WITH CONTACTLESS PISTON TO DISPENSE FORMULA

(71) Applicant: L'Oreal, Paris (FR)

(72) Inventors: Gregoire Charraud, Jersey City, NJ (US); Casey Barbarino, San Anselmo, CA (US); Rafael Feliciano, New Providence, NJ (US)

(73) Assignee: L'Oreal, Paris (FR)

( * ) Notice: Subject to any disclaimer, the term of this patent is extended or adjusted under 35 U.S.C. 154(b) by 230 days.

(21) Appl. No.: 17/732,036

(22) Filed: Apr. 28, 2022

(65) Prior Publication Data
US 2023/0346103 A1     Nov. 2, 2023

(51) Int. Cl.
*A45D 34/04*       (2006.01)
*A61N 5/06*         (2006.01)

(52) U.S. Cl.
CPC ......... *A45D 34/041* (2013.01); *A61N 5/0616* (2013.01); *A45D 2200/05* (2013.01); *A45D 2200/055* (2013.01); *A61N 2005/0658* (2013.01)

(58) Field of Classification Search
CPC .............. A45D 34/041; A45D 2200/05; A45D 2200/055; A61N 5/0616; A61N 2005/0658; A61N 2005/1061; A61N 5/1049
See application file for complete search history.

(56) References Cited

U.S. PATENT DOCUMENTS

| | | |
|---|---|---|
| 10,034,530 B2 | 7/2018 | Casasanta, III |
| 10,076,646 B2 | 9/2018 | Casasanta et al. |
| 10,405,638 B2 | 9/2019 | Streeter et al. |
| 10,695,582 B2 * | 6/2020 | Dunleavy ............. G06Q 20/22 |
| 10,842,241 B2 | 11/2020 | Casasanta, III |
| 10,939,740 B2 | 3/2021 | Cheng et al. |
| 11,126,955 B1 * | 9/2021 | Watson ............. G06Q 30/0633 |
| 11,457,719 B2 | 10/2022 | Streeter et al. |
| 2005/0131427 A1 | 6/2005 | Saito et al. |
| 2015/0360014 A1 | 12/2015 | Decaux et al. |
| 2019/0029917 A1 * | 1/2019 | George ............... A61H 9/0007 |
| 2020/0205547 A1 | 7/2020 | Cheng et al. |
| 2022/0160586 A1 * | 5/2022 | Ozolins .................... G08B 7/06 |

FOREIGN PATENT DOCUMENTS

| | | |
|---|---|---|
| KR | 20100132295 A | 7/2011 |
| KR | 20180099003 A | 9/2018 |
| WO | 2014091035 A1 | 6/2014 |
| WO | 2015193303 A1 | 12/2015 |
| WO | 2016146778 A1 | 9/2016 |

OTHER PUBLICATIONS

Search Report and Written Opinion mailed Jan. 31, 2023, issued in French Application No. 22 06390, filed Jun. 27, 2022, 6 pages.
International Search Report and Written Opinion mailed Jun. 27, 2023, issued in corresponding International Application No. PCT/US2023/017525, filed Apr. 5, 2023, 14 pages.

* cited by examiner

*Primary Examiner* — Donnell A Long
(74) *Attorney, Agent, or Firm* — CHRISTENSEN O'CONNOR JOHNSON KINDNESS PLLC

(57) ABSTRACT

An applicator comprising a reservoir configured to hold a formula, a roller ball configured to apply the formula, a contact-less piston, configured to dispense the formula, and a piston magnet disposed underneath the contact-less piston, wherein the piston magnet is configured to move the piston in response to a magnetic field.

20 Claims, 4 Drawing Sheets

ROLLER BALL APPLICATOR WITH CONTACTLESS PISTON TO DISPENSE FORMULA

SUMMARY

The following describes a system for applying a formula with an applicator having a contactless piston for distributing a skin care formula in a quiet, cost-effective, and efficient manner, as well as a mechanism for accurately measuring the amount of formula still present in the applicator.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, an applicator comprising a reservoir configured to hold a formula, a roller ball configured to apply the formula, a contact-less piston, configured to dispense the formula, and a piston magnet disposed underneath the contact-less piston, wherein the piston magnet is configured to move the piston in response to a magnetic field is disclosed.

In another aspect, a system for dispensing a formula, the system including an applicator including a reservoir configured to hold a formula, a contact-less piston, configured to dispense the formula, a piston magnet disposed underneath the contact-less piston configured to move the piston in response to a magnetic field, a roller ball configured to apply the formula, and an attachment for connecting to a dispensing device, and a dispensing device configured to connect to the applicator and administer a light treatment is disclosed.

In yet another aspect, a method of dispensing a formula, the method including attaching an applicator filled with a formula to a dispensing device, identifying the formula by reading the contactless chip on the applicator with a contactless reader on the dispensing device, generating a magnetic field with one or more magnets, wherein the magnetic field moves a piston magnet connected to a piston, and dispensing the formula as the piston moves is disclosed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Described herein is an applicator with a contactless piston for distributing and applying a formula to a surface with a roller ball. In some embodiments, the applicator also includes a mechanism for precisely detecting how much product is inside the applicator.

In some embodiments, the applicator is configured to attach to a dispensing device. In some embodiments, the dispensing device is configured to administer light therapy while applying the formula.

Figure 1A:
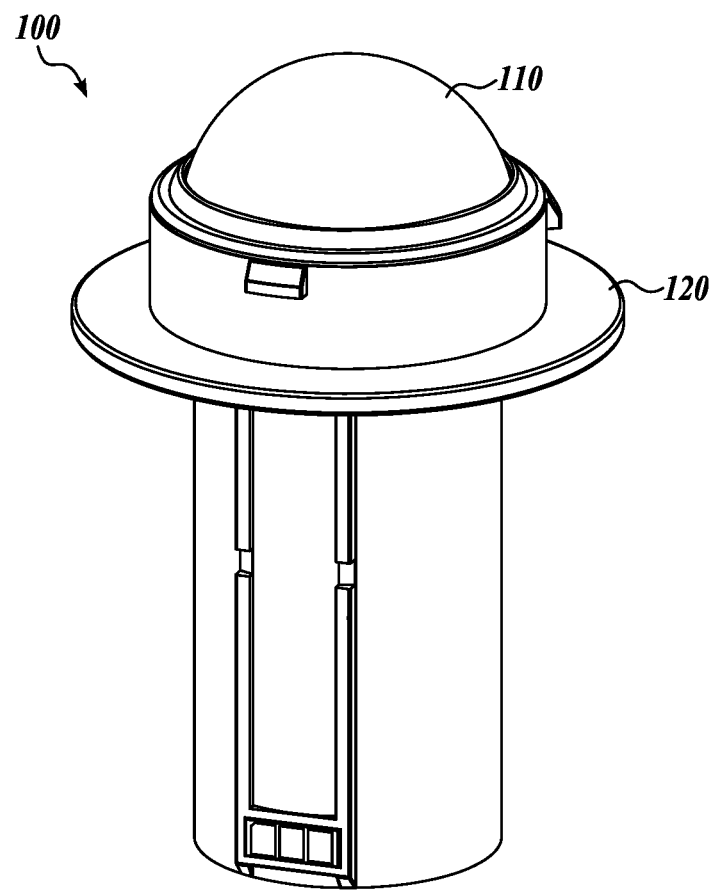
FIG. 1A is an example applicator, in accordance with the present technology.

FIG. 1A is an example applicator, in accordance with the present technology. The applicator 100 may include a roller ball 110, and an attachment 120.

Figure 1B:
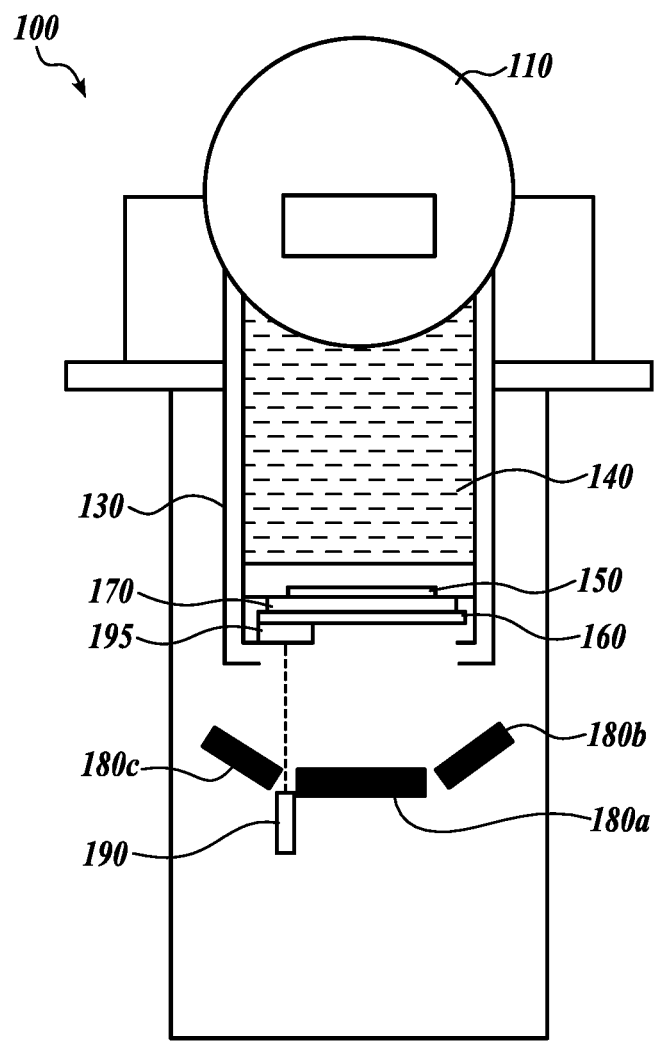
FIG. 1B is a cross section of the example applicator of FIG. 1B, in accordance with the present technology.

The roller ball 110 may be configured to distribute and apply a formula located a reservoir inside the applicator 100 (as shown in FIG. 1B). In some embodiments, the roller ball 110 is plastic, but in other embodiments, the roller ball 110 may be glass or metal.

Figure 2:
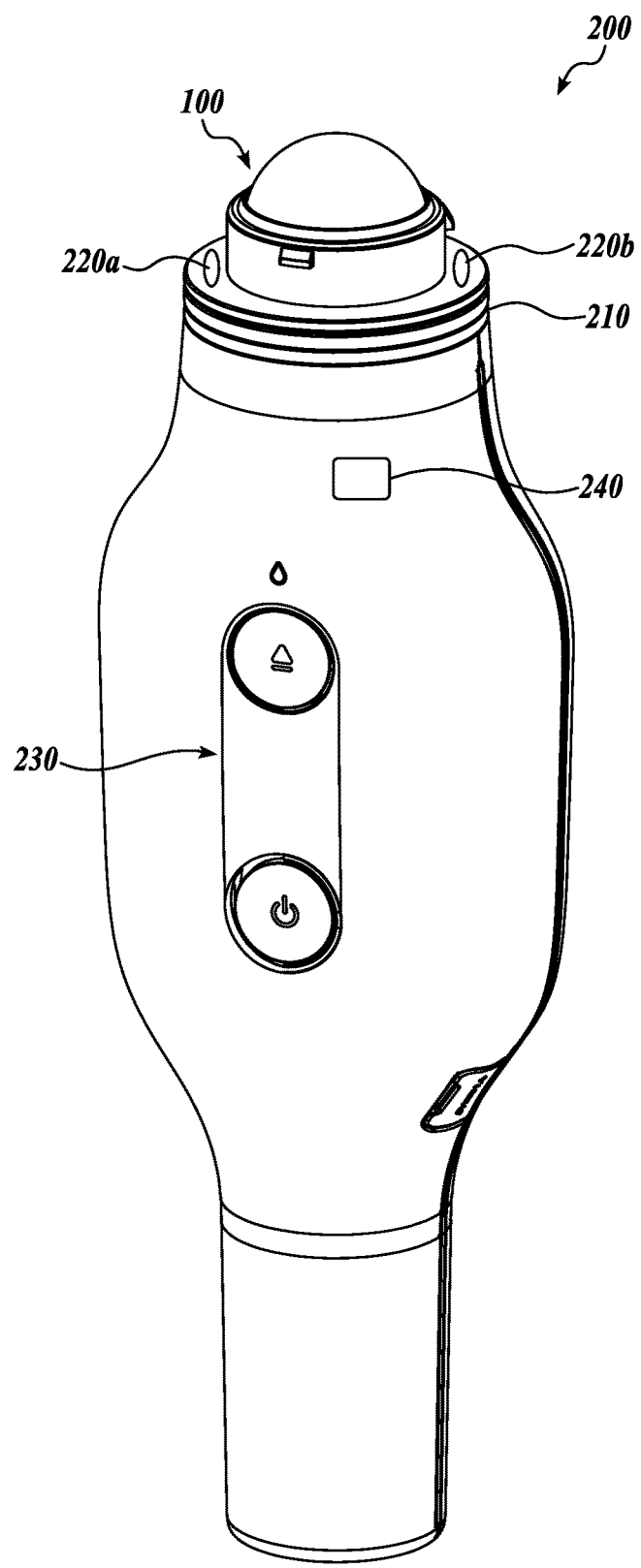
FIG. 2 is an example system including a dispensing device 200 with an example applicator 100 attached, in accordance with the present technology.

In some embodiments, the applicator 100 also includes an attachment 120 configured to secure the applicator 100 into a dispensing device, such as the dispensing device 200 in FIG. 2. While the attachment 120 is illustrated as one or more tabs to couple to a dispensing device, the attachment 120 may take any form capable of securing the applicator to a dispensing device including a threaded attachment, a magnet, or an attachment configured to snap or slide into the dispensing device. In some embodiments, the attachment 120 is clear so that the dispensing device is visible through the attachment.

In operation, the applicator 100 can be placed inside a dispensing device (as shown in FIG. 2) and secured to the dispensing device with the attachment 120. The roller ball 110 can be rolled over a surface, such as a user's skin, to apply a formula.

FIG. 1B is a cross section of the applicator of FIG. 1A, in accordance with the present technology. The applicator 100 may include a roller ball 110, a reservoir 130 configured to hold a formula 140, a piston 150, a contactless chip 160, a piston magnet 170, and one or more magnets 180a, 180b, 180c.

In some embodiments, the reservoir 130 is located inside the applicator 100, and is configured to hold a formula 140. In some embodiments, the formula 140 is a skin care formula. In some embodiments, the skin care formula is a moisturizer, a toner, an acne treatment, a wrinkle or fine line treatment, or a cosmetic, such as a foundation or concealer. As the roller ball 110 rolls, formula 140 from the reservoir 130 is applied to a surface.

In some embodiments, the applicator 100 further includes a piston 150 configured to push the formula 140 towards the roller ball 110 as the formula is applied. In some embodiments, the piston 150 is directed by circuitry on a dispensing device (such as dispensing device 200 of FIG. 2) or on the applicator itself to push the formula 140 towards the roller ball 110.

In some embodiments, the piston 150 is driven upwards by a piston magnet 170. The piston magnet 170 may be located underneath the piston 150. The piston 150 may be pushed up with the piston magnet 170 in response to a magnetic field. While in some embodiments, the piston magnet 170 and the piston 150 are two separate component, but in other embodiments, the piston magnet 170 and the piston 150 are a single component. In some embodiments, the piston magnet 170 is located within the piston 150. In some embodiments, the piston 150 is comprised of plastic, and it encapsulates the piston magnet 170. In some embodiments, the piston magnet 170 is not removable. In some embodiments, the piston can be 150 can be precisely positioned for better control.

In some embodiments, the applicator 100 includes one or more magnets 180a, 180b, 180c to generate the magnetic field. In some embodiments, the one or more magnets 180a, 180b, 180c are a first magnet 180a, a second magnet 180b, and a third magnet 180c. As illustrated, in some embodiments, the first magnet 180a is parallel to the piston magnet 160. In some embodiments, the second magnet 180b is disposed at a 45-degree angle to the right of the first magnet 180b, and the third magnet 180c are disposed at a 45-degree angle to the left from the first magnet 180b. While this configuration is illustrated, it should be appreciated that the one or more magnets 180a, 180b, 180c can take any configuration that would generate a magnetic field. While the one or more magnets 180a, 180b, 180c are illustrated as inside the applicator, in some embodiments, the one or more magnets 180a, 180b, 180c are inside a dispensing device, such as dispensing device 200 in FIG. 2.

In some embodiments, the applicator 100 includes a contactless chip 160 configured to identify the type of formula 140 inside the applicator 100 to a dispensing device. The contactless chip 160 may be used to identify any number of things about the formula 140 or applicator 100, including the amount of formula 140 inside the applicator 100, the expiration date of the formula 140 inside the applicator 100, or when to replace the applicator 100.

In some embodiments, the applicator 100 further includes a mechanism 190, 195 for measuring how much formula 140 is inside the reservoir 130. In some embodiments, the mechanism includes a time-of-flight sensor 190, and mirror coating 195 inside the reservoir 130. In some embodiments, the time-of-flight sensor 190 is located inside the applicator 100, but the time of flight sensor 190 may also be located inside a dispensing device (such as dispensing device 200 in FIG. 2).

In operation, the time-of-flight sensor 190 is configured to emit an LED light, illustrated as a dashed line. The mirror coating 195 is configured to reflect the LED light into the time of flight sensor 190. While the time-of-flight sensor 190 is illustrated as being directly underneath the mirror coating 195, in some embodiments, the time-of-flight sensor may be farther from the mirror coating 195, such that one or more reflectors (not pictured in FIG. 1B) reflect the emitted LED to the mirror coating 196 and back to the time-of-flight sensor 190.

FIG. 2 is an example system including a dispensing device 200 with an example applicator 100 attached, in accordance with the present technology. In some embodiments, the applicator 100 can be attached to a dispensing device 200. In some embodiments, the dispensing device includes an end 210, one or more light sources 220a, 220b, an actuator 230, and a contactless reader 240. In some embodiments, the applicator 100 connects to the dispenser 200.

In some embodiments, the dispensing device 200 includes an end 210. The end 210 may be configured to be seen through the attachment 120 on the applicator 100. In some embodiments, the base 210 includes one or more light sources 220a, 220b configured to administer light treatment to a surface while the formula is being applied.

In some embodiments, the one or more light sources 220a, 220b are LEDs. In some embodiments, there are only two light sources 220a, 220b on the dispensing device. In some embodiments, a first light source 220a is configured to administer light therapy in a first wavelength. In some embodiments, a second light source 220b is configured to administer light therapy in a second wavelength. In some embodiments, the light therapy in the first wavelength and the light therapy in the second wavelength are administered simultaneously. In some embodiments, the light therapy and applying the formula happen simultaneously.

In some embodiments, the dispensing device 200 includes one or more actuators 230. While the actuator 230 is illustrated as a button, in some embodiments, the actuator may be a switch, a capacitive touch type button, a dial, or the like. The actuator may be configured to begin the administration of light therapy, to apply the formula, or both.

In some embodiments, the dispensing device 200 also includes a contact-less chip reader 230 to read the contactless chip 160 on the applicator 100.

In operation, a user may place an applicator 100 into the dispensing device 200. When the actuator 230 is actuated, the formula is applied, the light therapy is administered, or both, simultaneously. A user may then apply the formula with the applicator 100.

Figure 3:
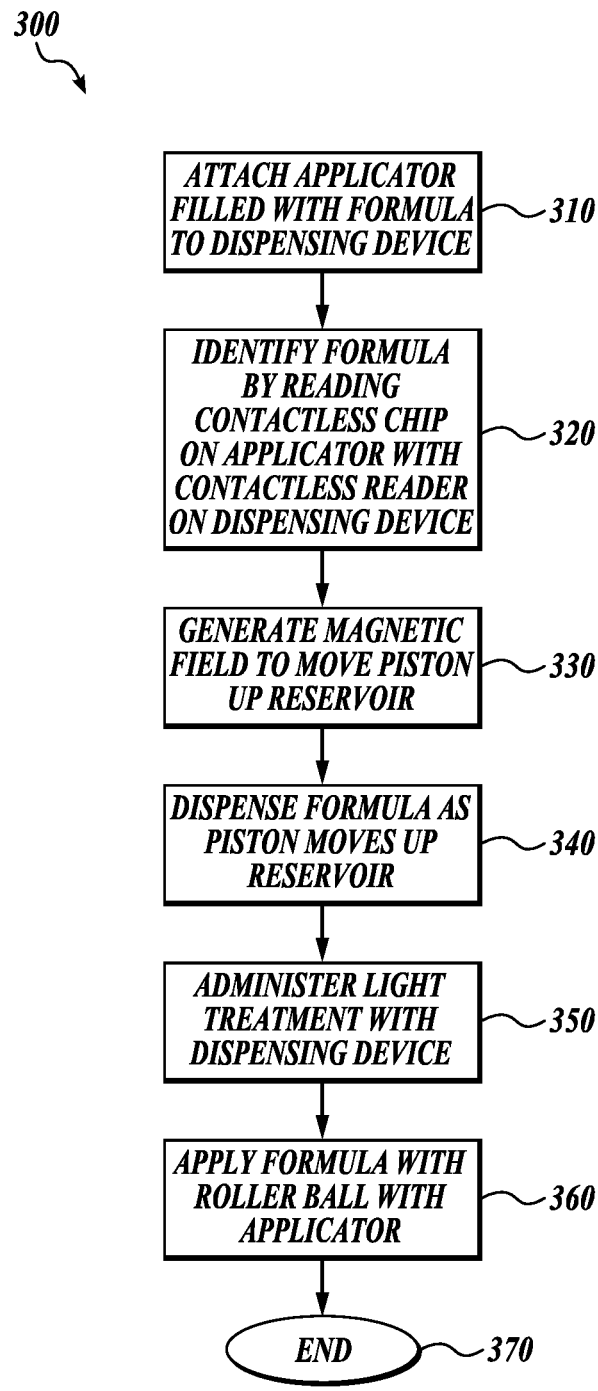
FIG. 3 is an example method of using a skin care system, in accordance with the present technology.

FIG. 3 is an example method 300 of using a skin care system, in accordance with the present technology.

In block 310, the applicator is attached to the dispensing device. In some embodiments, the applicator is slid into the dispensing device. In some embodiments, the applicator clicks into place inside the applicator. In some embodiments, the applicator is secured to the dispensing device through a snap, tab, or magnet.

Optionally, in block 320, a contactless reader on the dispensing device identifies the formula inside the applicator with the contactless chip on the applicator. In some embodiments, the contactless chip may also identify the amount of formula inside the applicator or whether or not the applicator needs to be replaced.

In block 330, the magnetic field is generated to move the piston magnet, and therefore the piston, up the reservoir to push the formula towards the roller ball. In some embodiments, the magnetic field is generated by one or more magnets inside the applicator. In some embodiments, the magnetic field may be generated by the dispensing device. In some embodiments, the magnetic field is generated by a first, second, and third magnet. As the magnetic field is generated, the piston magnet pushes the piston to move the formula towards the roller ball.

In block 340, the formula is dispensed as the piston is pushed up the reservoir. As the piston pushes up, the formula is pushed towards the roller ball.

In block 350, the dispensing device administers light treatment. In some embodiments, the dispensing device administers a light treatment with one or more light sources. In some embodiments, the dispensing device may be configured to administer one or more light therapies. In some embodiments, one or more light sources on the dispensing device are configured to administer a first light therapy at a first wavelength, and one or more light source are configured to administer a second light therapy at a second wavelength. In some embodiments, the first light therapy and the second light therapy are administered consecutively, but in other embodiments, the first and second light therapy are administered concurrently.

In block 360, the roller ball is rolled over a surface, such as a user's skin, the formula is applied to the surface. In some embodiments, steps 330-360 all occur simultaneously.

In block 370, the method ends.

The embodiments of the invention in which an exclusive property or privilege is claimed are defined as follows:

1. An applicator comprising:
    a reservoir configured to hold a formula;
    a roller ball configured to apply the formula;
    a contact-less piston, configured to dispense the formula;

a time-of-flight sensor configured to detect the amount of formula inside the applicator;
an LED, wherein the LED emits a light inside of the applicator configured to reflect off the piston and into the time-of-flight sensor; and
a piston magnet disposed underneath the contact-less piston, wherein the piston magnet is configured to move the piston in response to a magnetic field.

2. The applicator of claim 1, wherein the applicator further includes mirror coating on the piston, wherein the mirror coating is configured to reflect the LED into the time-of-flight sensor.

3. The applicator of claim 1, wherein the applicator further comprises one or more magnets located in the body of the applicator, wherein the one or more magnets generate the magnetic field to control the contact-less piston.

4. The applicator of claim 3, wherein the one or more magnets comprises a first magnet, a second magnet, and a third magnet.

5. The applicator of claim 4, wherein the first magnet is parallel with the piston magnet.

6. The applicator of claim 4, wherein the second magnet and the third magnet are disposed at a 45-degree angle from the first magnet.

7. A system for dispensing a formula, the system comprising:
an applicator comprising:
a body,
a reservoir configured to hold a formula,
a contact-less piston, configured to dispense the formula,
a time-of-flight sensor configured to detect the amount of formula inside the applicator,
an LED, wherein the LED emits a light inside of the applicator configured to reflect off the piston and into the time-of-flight sensor,
a piston magnet disposed underneath the contact-less piston configured to move the piston in response to a magnetic field,
a roller ball configured to apply the formula, and
an attachment for connecting to a dispensing device; and
a dispensing device configured to connect to the applicator and administer a light treatment.

8. The system of claim 7, wherein the light treatment is administered simultaneously with the application of the formula.

9. The system of claim 7, wherein the applicator further comprises one or more magnets located in the body of the applicator, wherein the one or more magnets generate the magnetic field to control the contact-less piston.

10. The system of claim 7, wherein the applicator further comprises a contactless chip configured to identify the formula inside the applicator.

11. The system of claim 10, wherein the dispensing device further includes a contactless reader to read the contactless chip on the applicator.

12. The system of claim 7, wherein the dispenser further comprises two or more light sources, and wherein light therapy comprises:
emitting light having a first wavelength with one light source of the two or more light sources; and
emitting light having a second wavelength with another light source of the two or more light sources.

13. The system of claim 7, wherein the dispenser further comprises an actuator.

14. A method of dispensing a formula, the method comprising:
attaching an applicator filled with a formula to a dispensing device;
identifying the formula with a contactless reader on the applicator;
generating a magnetic field with one or more magnets, wherein the magnetic field moves a piston magnet connected to a piston;
measuring the amount of formula inside the applicator at a given time, comprising:
shining an LED inside the applicator;
reflecting a light generated by the LED off a mirror coating inside the applicator; and
determining the amount of formula inside the applicator based on the time taken to reflect the light off the mirror coating; and
dispensing the formula as the piston moves.

15. The method of claim 14, wherein the method further comprises administering a light treatment.

16. The method of claim 15, wherein the method further comprises administering the light treatment and dispensing the formula simultaneously.

17. The method of claim 14, wherein the method further comprises administering a light treatment in the form of emitting two or more wavelengths simultaneously.

18. The method of claim 17, wherein the method further comprises administering a light treatment in the form of emitting two or more wavelengths consecutively.

19. The method of claim 14, wherein the method further comprises applying the formula to a surface with a roller ball.

20. The method of claim 14, wherein the method further comprises actuating an actuator on the dispensing device to generate the magnetic field.

* * * * *